United States Patent [19]

Lesko et al.

[11] Patent Number: 5,133,210
[45] Date of Patent: Jul. 28, 1992

[54] THERMAL EXPANSION DRIVEN INDENTATION STRESS-STRAIN SYSTEM

[75] Inventors: John J. Lesko, Blacksburg, Va.; Ronald W. Armstrong, Edgewater, Md.

[73] Assignee: The University of Maryland, College Park, Md.

[21] Appl. No.: 475,453

[22] Filed: Feb. 6, 1990

[51] Int. Cl.$^5$ .......................... G01N 3/42; G01N 3/54
[52] U.S. Cl. ........................................ 73/81; 374/46
[58] Field of Search ................. 73/81, 83, 85; 374/46, 374/53

[56] References Cited

U.S. PATENT DOCUMENTS

| | | | |
|---|---|---|---|
| 2,535,830 | 12/1950 | Beck | 374/46 |
| 3,693,417 | 9/1972 | Fritz et al. | 73/81 |
| 3,855,848 | 12/1974 | Sidler | 73/81 |
| 3,934,463 | 1/1976 | Venderjagt | 73/81 |
| 3,939,700 | 2/1976 | Anderson | 73/83 |
| 4,136,555 | 1/1979 | Iwasaki | 73/83 |
| 4,182,164 | 1/1980 | Fohey | 73/83 |
| 4,304,123 | 12/1981 | Aschinger et al. | 73/81 |
| 4,312,220 | 1/1982 | Borgersen et al. | 73/81 |
| 4,331,026 | 5/1982 | Howard et al. | 73/81 |
| 4,354,764 | 10/1982 | Achemann et al. | 374/46 X |
| 4,361,034 | 11/1982 | Borgersen et al. | 73/81 |
| 4,367,961 | 1/1983 | Griffin | 374/46 |
| 4,445,367 | 5/1984 | Goldsmid | 73/81 |
| 4,450,713 | 5/1984 | Arimatsu | 73/81 |
| 4,530,235 | 7/1985 | Shabel | 73/81 |
| 4,534,212 | 8/1985 | Targosz | 73/83 |
| 4,611,487 | 9/1986 | Krenn et al. | 73/81 |
| 4,621,523 | 11/1986 | Shabel et al. | 73/81 |
| 4,699,000 | 10/1987 | Lashmore et al. | 73/81 |
| 4,711,587 | 12/1987 | Couto | 374/46 X |
| 4,773,258 | 9/1988 | Kiffe | 73/81 |
| 4,820,051 | 4/1989 | Yanagisawa et al. | 73/81 X |
| 4,956,994 | 9/1990 | Lue | 73/81 |

FOREIGN PATENT DOCUMENTS

| | | | |
|---|---|---|---|
| 38182 | 12/1970 | Japan | 374/53 |
| 94137 | 7/1980 | Japan | 73/81 |
| 89729 | 5/1985 | Japan . | |
| 340932 | 6/1972 | U.S.S.R. | 374/46 |
| 813190 | 3/1981 | U.S.S.R. | 374/46 |
| 918814 | 4/1982 | U.S.S.R. | 374/46 |

OTHER PUBLICATIONS

*Patent Abstracts of Japan* Grp. p. 390; vol. 9, No. 236; ABS pub. date Sep. 21, 1985 (60-89729).

*Primary Examiner*—Tom Noland
*Attorney, Agent, or Firm*—Oblon, Spivak, McClelland, Maier & Neustadt

[57] ABSTRACT

Disclosed is a method and apparatus of indentation testing of variable types of specimens which includes mounting an indenter member onto a thermally expandable member, mounting the specimen to be tested on a pedestal, loading the specimen with the indenter member by thermally expanding the thermally expandable member and measuring applied force to and displacement of the specimen so as to determine the hardness or other material properties of the specimen. The indenter member is thermally insulated from the thermally expandable member prior to thermally expanding the thermally expandable member. The thermal expansion driven indentation system in the present invention allows for controlled application of precise and continuous reproducible loads to produce stress-strain plots. Continuous indentation testing with this system has yielded results which correlate well to Rockwell fixed load hardness tests on standard test blocks. Further, efforts in drawing relationships with tensile results have shown support for the use of continuous indentation testing for the generation of local material properties.

12 Claims, 4 Drawing Sheets

THERMAL EXPANSION DRIVEN INDENTATION STRESS-STRAIN SYSTEM

BACKGROUND OF THE INVENTION

1. Field of the Invention

The present invention is directed to a thermal expansion driven indentation system which allows for controlled application of reproducible precise and continuous loads for the production of stress-strain information. The continuous indentation system in accordance with the present invention adapts well to the generation of load versus penetration depth plots during hardness testing. Continuous indentation tests on high strength steel reveals very close comparisons with conventional fixed load Rockwell test results, and tensile test results.

2. Background of the Discussion

Conventional fixed load hardness tests (i.e. Rockwell, Birnell, etc.) do not provide measurements of well defined material properties. The values generated by these tests only supply relative information about a material's resistance to indentation and/or an indication of the specimen's heat treatment. Further, elastic material which surrounds the plastic zone of the indentation acts to hinder plastic flow. Exploring the combined elastic and plastic deformation behavior during hardness testing would allow for the deduction of the elastic contribution to the final plastic indentation. Thus, useful information can be resolved from hardness testing if load and penetration depth are continuously monitored during indentation. Previous working systems in this area have employed an Instron testing machine (with modified grips) to generate stress-strain relationships of various materials. While promising results have been obtained, machine compliance became a problem when reaching higher loads. Thus, it has become desirable to develope a device which is suited for the application of continuous and precise loads to finally generate a stress-strain relationship.

SUMMARY OF THE INVENTION

An object of the present invention has been to provide a system which utilizes controlled thermal expansion to drive a continuous indentation so as to overcome the drawbacks of the prior art. Depending upon the amount of heat incident on an expansion member, a suitable range of displacements can be generated for material indentation purposes.

In accordance with the present invention, the thermal expansion driven indentation system allows for the controlled application of reproducible precise and continuous loads to produce stress-strain information. Continuous indentation testing with the system has yielded results which correlate quite well to Rockwell fixed load hardness tests on high strength steel. Further, efforts in drawing relationships with tensile results have shown support for the use of continuous indentation testing for the generation of local material properties.

It has been found that in accordance with the present invention, the continuous indentation system lends itself well to the generation of load versus penetration depth relationship during hardness testing. Because it relies on the thermal expansion of a metal rod, there are fewer moving parts which thus provides the device with little or no problems with compliance. Moreover, the delicate loads and displacements that can be generated by this type of device lends itself well to accurate use in the elastic region of a material's behavior. Continuous indentation trials on high strength steel test blocks reveal a very close comparison with conventional fixed load Rockwell test results. Also, correlation to tensile test results show support for the use of continuous indentation testing to provide information on defined material properties. The system could ultimately assist in supplying information on a material's local properties within a particular region.

To the knowledge of the inventors, no one has to date employed thermal expansion as a controlled method of obtaining accurate reproducible indenter displacements. In accordance with the present invention displacements in the range of 0.1 to 125 $\mu$m are easily achievable. The obtainment of a continuous record of indentation force versus displacement for a spherical indentation provides a hardness stress-strain record for a local region of the indented material. In accordance with the present invention, rather than attempting to assess the "relative" material property from a single indentation size produced by a fixed indenter load, the current tester used in accordance with the present invention provides a continuous load versus indentation size record. The relatively large value of thermal expansion coefficient, e.g. $2 \times 10^{-5}$ cm/cm °C. for Al, allows easily controlled displacements with modest temperature changes—to cover the elastic and plastic responses of the material being tested. With respect to possible application of the technology disclosed in the present invention, in the near term, continuous indentation testers covering various displacement and load scales could be developed for a variety of material specimen shapes and sizes. In addition, a portable tester could be designed for in-service material evaluation of engineering structures. A repeated loaded-unloaded indentation sequence could be designed to evaluate the compression-fatigue and internal friction properties of a material specimen. It is further noted that the system has been used to measure the creep-related indentation response of polymeric materials.

It should also be noted that the test system used in accordance with the present invention can be employed to measure the applied force and displacement for propagating one or more cracks into pre-cracked specimens, involving the methods of indentation fracture mechanics. In addition, a coolant system can be employed to drive a contracting rod so as to produce an indentation in a specimen held within a yoke frame.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein.

DESCRIPTION OF THE PREFERRED EMBODIMENT

Figure 1:
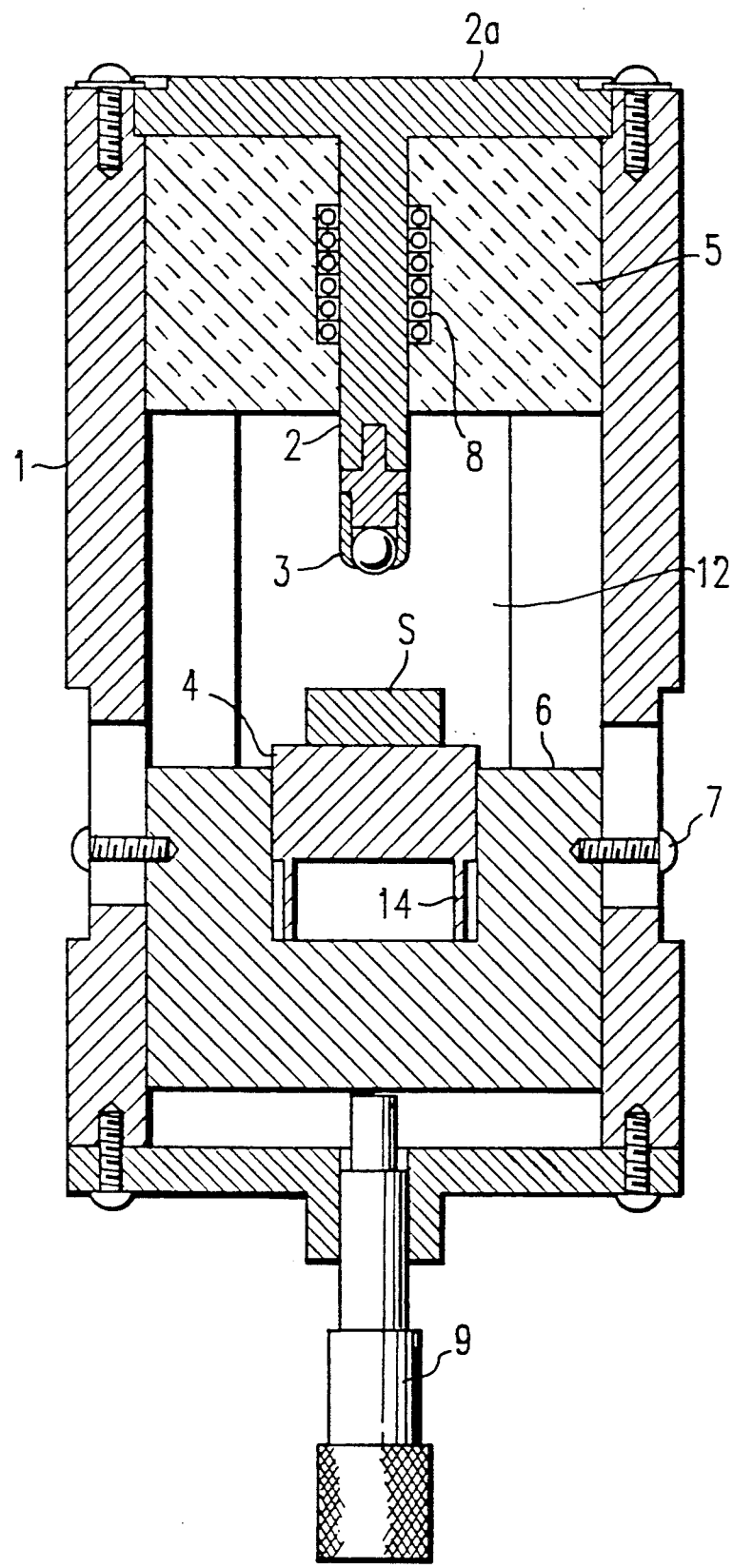
FIG. 1 shows a sectional view of the continuous indentation hardness tester in accordance with the present invention.

The indenter system and method of use of the indenter system will now be described. The indenter system may be housed in a ⅛ inch walled 3 & ⅜ inch outer diameter steel tube type support structure 1, as best shown in FIG. 1. The thermal expansion member is a rod 2 incorporated into a flange 2a wherein the flange 2a is rigidly affixed to the top of the support structure 1. Rod 2 has an indenter head 3. An AC coiled cable heater 8 is wrapped around a 1 inch section midway of the length of rod 2. The heater 8 is controlled by a variable AC transformer (not shown) and can reach temperatures as high as 300° C. A temperature of approximately 200° C. is reached when generating a 10 to 20 kilogram force load on the specimens with about 80 to 100 micrometers of displacement. The heater 8 is sufficiently insulated with a porous ceramic to prevent radiative and convected heat transfer to support structure 1. Heater 8 is surrounded by insulation 5. Heat conduction through the flange 2a and indenter rod 2 is minimal when indentations occur between adequately spaced time periods.

The sample or specimen S is positioned on a subpedestal 4 having a thin walled tube load cell 14 positioned on a main pedestal 6. Also used is a micrometer 9 to adjust the position of main pedestal 6 with respect to indenter head 3. Locking screw trace 7 serves to lock main pedestal 6 in position with respect to the support 1 once positioning of indenter head 3 with respect to the surface of the specimen S has been accomplished. Viewing window 12 is also shown.

Figure 2:
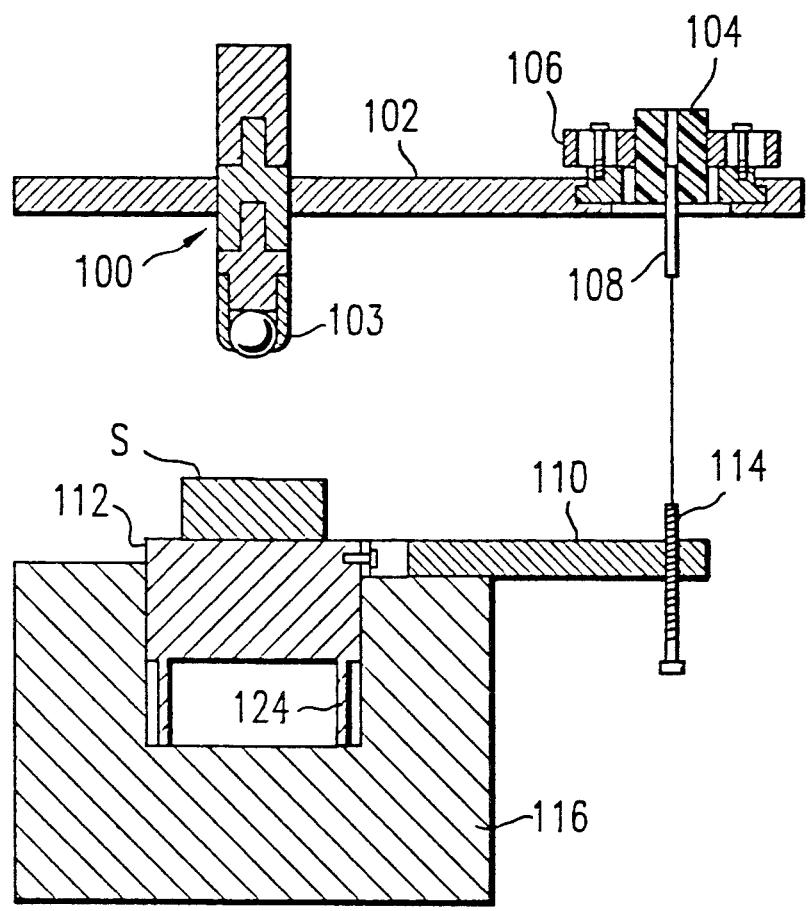
FIG. 2 shows a load and displacement transducer assembly.

Shown in FIG. 2 is a sectional view of a displacement transducer assembly for testing load and penetration of the specimen but without showing the support structure, for ease of illustration, utilized with the structure of FIG. 1. This includes Rockwell indenter head 103 which is inserted into an adapter 100, machined from Inconel, which serves two purposes. First, it provides thermal isolation from the rod to prevent heating of the indenter head 103. Second, the adapter 100 furnishes a point at which an upper cantilever 102 can be affixed for support of a displacement transducer 104 (HP 24DCDT-050(C)). An X-Y translator 106 is connected to the cantilever 102 for positioning of the transducer coils 104, without contact with a magnetic core 108. A lower cantilever 110 is affixed to the subpedestal portion of the specimen load cell 112 for support of a Z-translator screw 114 and which controls Z translation of the core 108. The placement of main pedestal 116 can be adjusted with respect to the location of indenter head 103 by means of a micrometer screw contacting the main pedestal 116 in a manner similar to that shown in FIG. 1. When positioning of the indenter head 103 with respect to the surface of the specimen S is accomplished, the pedestal 116 can be locked rigidly into place by locking screws like those used in FIG. 1.

Once the specimen S is positioned and the main pedestal 116 is locked into place, the indenter head 103 can be driven by the rod. Discontinuation of heating of the rod causes the rod to cease expansion and begins unloading of the indentation of the specimen S. Retrieval of the specimen S is accomplished by unlocking the screws and lowering the main pedestal 116 in the same manner as in FIG. 1.

As shown in FIGS. 1 and 2, a thin-walled cylindrical base which serves as a load cell (14, 124) is part of a subpedestal (112) upon which specimen S is placed. The main pedestal support base can be positioned as desired relative to the indenter head. Displacement is measured with the linear variable differential transformer (LVDT) system (104 and 108) as shown in FIG. 2. The force-displacement record is fed into a data acquisition system or X-Y plotter to obtain the results shown, for example, in FIG. 3.

Experimental indentation results have been obtained on HSLA 80 steel material whose conventional stress/strain behavior has been described (by Gudas) and on related weldment material whose conventional hardness and stress/strain behavior has been described (by Scoonover).

Figure 3:
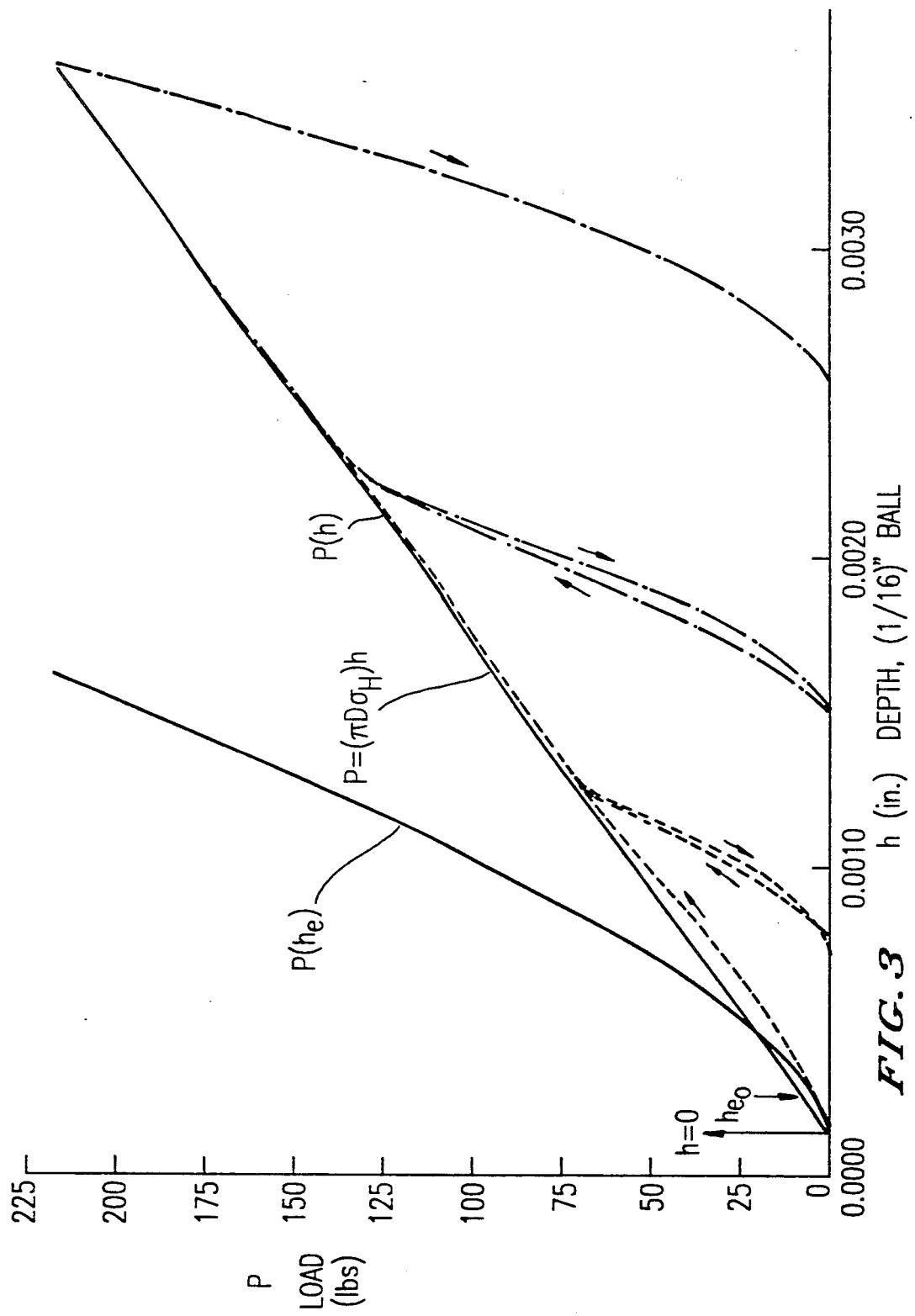
FIG. 3 has a comparison of continuous load versus indenter penetration.

A continuous record of load, P, versus penetration depth, h, is shown in FIG. 3 for a (1/16) inch ball pressed into an HSLA 80 material specimen in three stages: first, continuously loaded to approximately 65 lbs and unloaded; then, immediately reloaded to approximately 130 lbs and unloaded; and finally, reloaded to 220 lbs and unloaded. Such records were obtained on an Instron testing machine (confirmed on the thermal expansion indentation system) with either an optical fiber or capacitance gauge for measuring the displacement between the ball and specimen surface.

The point of initial loading, h=0, is shown in FIG. 3 and the initial elastic deformation behavior of the ball and specimen is able to be followed up to a "yield point" at a relatively small load of approximately 4 lbs, corresponding to a displacement of approximately $1.1 \times 10^{-4}$ in.

The theoretical elastic curve for the $P\{h_e\}$ dependence on penetration is shown in FIG. 3 in accordance with the classical description given by Hertz, as verified previously with the expression:

$$P = \left[ \left( \frac{8D}{9} \right)^{\frac{1}{2}} \left( \frac{E_1 E_2}{(1 - \nu_1^2) E_2 + (1 - \nu_2^2) E_1} \right) \right] h_e^{3/2} \quad (1)$$

where P is applied load, D is the indenter ball diameter for material 1 and the subscripted E and $\nu$ symbols are for the Young's modulus and Poisson's ratio, respectively, for the ball and test specimen materials. For equation (1), D=(1/16) in., $E_1 = E_2 = 30 \times 10^6$ psi and $\nu_1 = \nu_2 = 0.28$, to obtain the elastic curve that is shown in FIG. 3. The machine deformation appears to be negligible, at least, in the early stages of the indentation test.

At relatively large elastic/plastic penetrations, $P\{h\}$ is found experimentally to be very nearly linearly dependent on h, as shown by the straight line equation in FIG. 3. This condition may be expressed as $$P = (\pi D \sigma_H) h \quad (2)$$

where $\sigma_H$ is known as the Meyer hardness for a rigid ball/rigid plastic material being indented; $\sigma_H = P/A_p$, where $A_p$ is the projected area of the residual plastic indentation. For a spherical ball $$A_p = \pi (d_p/2)^2 = \pi h_p (D - h_p), \quad (3)$$

where $d_p$ is the residual diameter of the plastic impression and $h_p$ is its depth. For $(h_p/D) << 1.0$, equation (2) is obtained from the Meyer hardness definition, subject to the condition that $h_p = h$. The latter approximation may seem questionable on the basis of the unloading/reloading results shown in FIG. 3, however, the unloading/reloading displacements for a significant plastic indentation are mainly caused by a shape change at the bottom of the indentation rather than by alteration in $d_p$. This consideration relates also to the $h_e$ curve in FIG. 3 in that the $h_e$ curve applies for an initially flat specimen surface and increases sufficiently slowly with P as the indentation becomes plastic with an increased area contact that $h_e \approx h_{eo}$ for the fully plastic indentation.

A typical plot is shown in FIG. 3 for an indentation done on a high strength steel.

For a combined elastic/plastic indentation, it is proposed that:

$$\sigma_H = P/(A_e + A_p), \tag{4}$$

where $A_e$ is the elastic contact area. From the Hertzian description $$A_e = \pi(d_e/2)^2 = \pi h_e D/2. \tag{5}$$

By substitution in equation (4) for $A_e$ and $A_p$ from equations (5) and (3), respectively, $$\sigma_H = P/\pi D([h_e/2] + [h_p(1 - h_p/D)]). \tag{6}$$

For $h \geq h_e$, $h_e \approx h_{eo}$ in FIG. 1 and, also, $(h_p/D) << 1.0$, so that $$\sigma_H \approx P/\pi D([h_{eo}/2] + h_p). \tag{7}$$

With $h = h_p + h_e$, $$\sigma_H \approx P/\pi D(h - [h_{eo}/2]). \tag{8}$$

For most of the data shown in FIG. 3, $h >> h_{eo}$, and so equation (2) is obtained from equation (8) in agreement with the straight line that is drawn in the figure. A straight line drawn from $[h_{eo}/2]$, at P=0 in FIG. 3, to each point on the P{h} curve gives $\sigma_H$ as the slope value.

$$\sigma_\epsilon = \sigma_H/2.8 \tag{9}$$

and $$\epsilon_p \approx (1/5)(d_p/D). \tag{10}$$

From the $d_p/h_p$ relationship in equation (3)

$$\epsilon_p \approx (1/5)[(4h_p/D)(1 - h_p/D)]^{\frac{1}{2}} \tag{11}$$

where: $\sigma_H$ is the Meyer hardness for a rigid ball/elastic-plastic material being indented, $\epsilon_\sigma$ is flow stress, $\sigma_p$ is the indentation strain by a ball indenter, P=Applied Load, $d_p$=Indentation Plastic Diameter, D=Indenter Ball Dia., h=$h_{Elastic}$+$h_{Plastic}$=Total Penetration, $h_{eo}$=h@ yielding, $h_p$=Plastic Penetration, $d_p$=Plastic Diameter or residual indentation. Comparatively, similar points are generated by a conventional Rockwell hardness test and are also shown. As can be seen, these points fall along the same line.

$$\sigma_\epsilon = \sigma_H/2.8 \tag{9}$$

and $$\epsilon_p \approx (1/5)(d_p/D). \tag{10}$$

From the $d_p/h_p$ relationship in equation (3)

$$\epsilon_p \approx (1/5)[(4h_p/D)(1 - h_p/D)]^{\frac{1}{2}} \tag{11}$$

Figure 4:
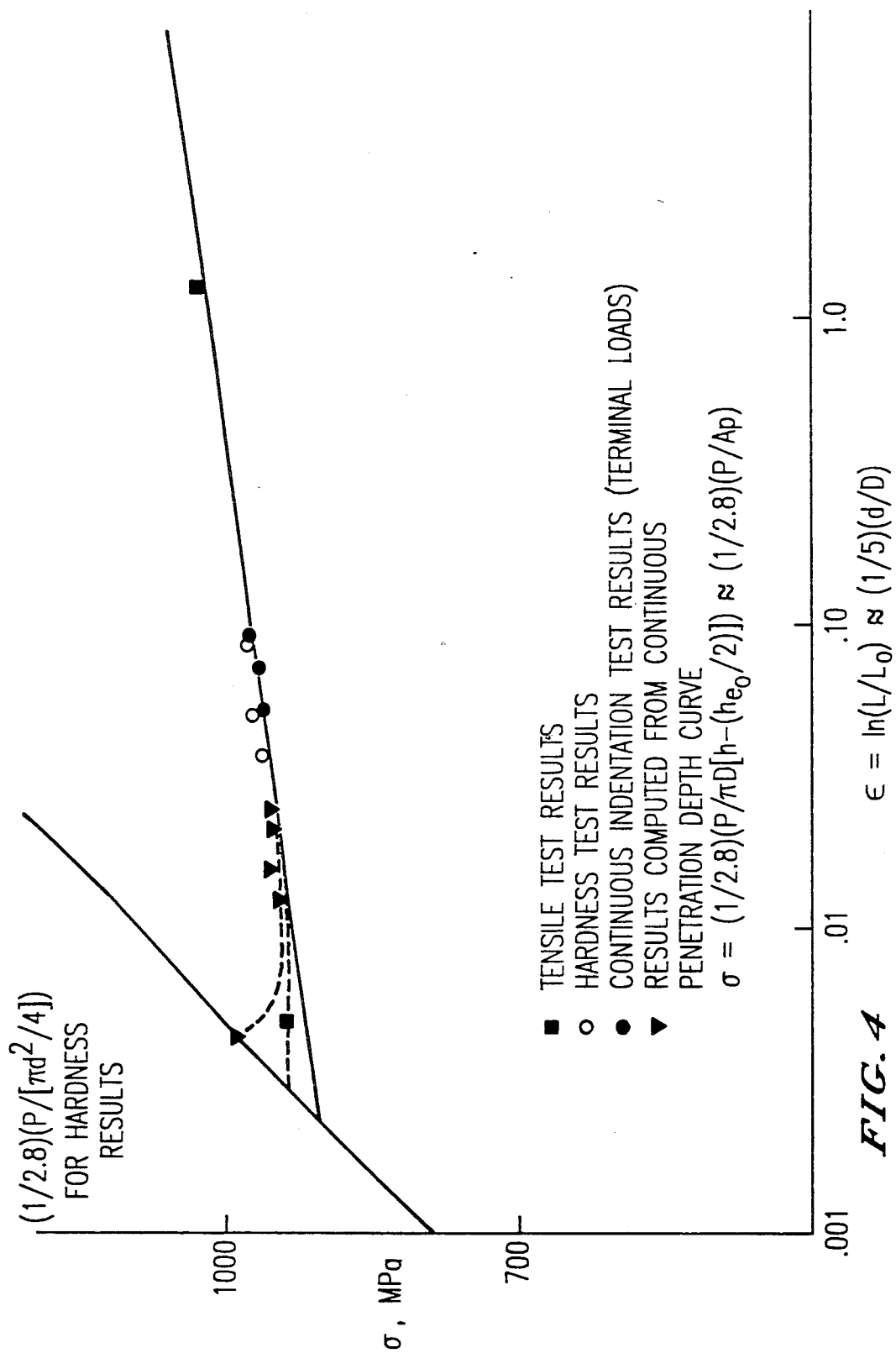
FIG. 4 shows a reduction of the continuous indentation information to tensile (stress/strain) information.

FIG. 4 shows computed stress/strain values, as indicated by the comparison with tensile test and conventional hardness values transformed to stress/strain values according to $\sigma_\epsilon = (\frac{1}{2}.8)P/A_p$. An elastic stress value, $\sigma_\epsilon = 134,700$ psi has been placed on the elastic loading line, using $\sigma_\epsilon = 2P/\pi D h_e$ with $P \approx 4$ lbs and $h_e = 1.1 \times 10^{-4}$ in. Five other paired $\sigma/\epsilon$ values have been computed using equations (8), (9) and (11), as applied to values of P=6.67, 10, 13.3 and 220 lbs. An elastic strain, $\epsilon_E$, value determined from the elastic loading line was added to each computed $\epsilon_p$ value, from equation (11), when plotted in FIG. 4. Very reasonable agreement is obtained between the various results. By reference to FIG. 3, it may be seen that an appropriate "slope value" at each point of the loading portion of the continuous indentation curve is a measure of the flow stress of the material at a corresponding strain point on style conventional $\sigma/\epsilon$ curve.

The above analysis has provided the primary means of evaluating the concept of thermal expansion driven continuous indention of ductile, isotropic and homogeneous materials. Given the instruments ability to produce delicate loads and displacements, and discern the elastic contribution to the indentation, many other applications are possible. For instance, brittle materials such as ceramics, and single crystals, may be tested to provide a continuous record of their elastic, plastic, and cracking responses. Such experiments have been undertaken on various planes of a silicon crystal. One continuous indentation can replace the need for running numerous (about 100) fixed load indentations to define all regimes of deformation. Likewise, polymers have been tested with the system. Polymers exhibit viscoeleastic properties (i.e., time dependent modulus, creep) and modified forms of plasticity untypical of metals. For a limited case, the reduction of a time dependent modulus from a continuous indentation has been demonstrated on a liner viscoelastic polymer. Conventionally, such data must come from a series of tensile creep tests conducted at various conditions to produce a "master curve" of the time dependent modulus. Further, the continuous indentation of multiple phase materials, such as fibrous composites could assist in the isolation of macro and/or micromechanical properties used in engineering these materials. Presently, the inventors are investigating the feasibility of measuring fiber/matrix interfacial properties in polymeric composites through continuous indentation.

Alternately, the continuous indentation system may also be programmed to run at various loading or displacement rates. Standard tests such as Rockwell, where minor and major loads are applied to a specimen at timed intervals and penetrations recorded, could be reproduced on the thermal expansion indentation system. Programmed tests could be very accurate and repeatable given the appropriate controlling hardware.

Obviously, numerous modifications and variations of the present invention are possible in light of the above teachings. It is therefore to be understood that within the scope of the appended claims, the invention may be practiced otherwise than as specifically described herein.

What is claimed is:

1. An indentation type tester, which comprises:
   a support member;
   a thermally expandable member connected to said support member and;

means connected to said thermally expandable member for indenting a specimen and which includes a ball-shaped indented head;

means connected to said support member for supporting said specimen to be tested, said specimen being supported between said means for supporting said specimen and said means for indenting said specimen;

means for heating said thermally expandable member and for driving said means for indenting said specimen so as to load said specimen; and means connected to said means for supporting said specimen, for measuring applied force and displacement of said specimen so as to determine at least one property of said specimen, said means for measuring applied force and displacement being separated from thermally expandable member.

2. A tester as claimed in claim 1, which comprises means for insulating said means for indenting said specimen from said thermally expandable member.

3. A tester as claimed in claim 1, which comprises an indenter rod wherein said ball-shaped indenter head is connected to an end portion of said indenter rod.

4. A tester as claimed in claim 1, wherein said thermally expandable member comprises a metal rod.

5. A tester as claimed in claim 1, wherein said means for heating said thermally expandable member comprises a heater ribbon which surrounds at least a portion of said thermally expandable member.

6. A tester as claimed in claim 1, which comprises means for locking and unlocking said means for supporting said specimen in position with respect to said support member.

7. A tester as claimed in claim 1, which comprises a subpedestal mounted on a pedestal and upon which said specimen is mounted.

8. A tester as claimed in claim 1, wherein said at least one property comprises the hardness of said specimen.

9. A tester as claimed in claim 1, wherein said specimen comprises a ductile material.

10. A tester as claimed in claim 1, wherein said specimen comprises one of a brittle material, a polymeric material and a multiple phase material.

11. A tester as claimed in claim 1, wherein said at least one property comprises one of an elastic, plastic and cracking property.

12. An indentation type tester, which comprises:

a support member;

a thermally expandable member connected to said support member and;

means connected to said thermally expandable member for indenting a specimen;

means connected to said support member for supporting said specimen to be tested, said specimen being supported between said means for supporting said specimen and said means for indenting said specimen;

means for heating said thermally expandable member and for driving said means for indenting a said specimen so as to load said specimen; and means connected to said means for supporting said specimen, for measuring applied force and displacement of said specimen so as to determine at least one property of said specimen, said means for measuring applied force and displacement being separated from thermally expandable member.

* * * * *